United States Patent
Leclere-Bienfait et al.

(10) Patent No.: US 11,484,559 B2
(45) Date of Patent: Nov. 1, 2022

(54) KAPOK TREE FLOWER EXTRACT, AND COSMETIC, PHARMACEUTICAL OR DERMATOLOGICAL COMPOSITIONS CONTAINING SAME

(71) Applicant: Laboratoires Expanscience, Paris la Défense (FR)

(72) Inventors: Sophie Leclere-Bienfait, Dreux (FR); Stéphanie Bredif, Croisilles (FR)

(73) Assignee: Laboratoires Expanscience

( * ) Notice: Subject to any disclaimer, the term of this patent is extended or adjusted under 35 U.S.C. 154(b) by 8 days.

(21) Appl. No.: 16/956,220

(22) PCT Filed: Dec. 21, 2018

(86) PCT No.: PCT/EP2018/086754
§ 371 (c)(1),
(2) Date: Jun. 19, 2020

(87) PCT Pub. No.: WO2019/122408
PCT Pub. Date: Jun. 27, 2019

(65) Prior Publication Data
US 2021/0093685 A1    Apr. 1, 2021

(30) Foreign Application Priority Data
Dec. 22, 2017 (FR) ...................... 1763152

(51) Int. Cl.
| | | |
|---|---|---|
| *A61K 36/185* | (2006.01) | |
| *A61K 8/9789* | (2017.01) | |
| *A61K 8/365* | (2006.01) | |
| *A61Q 19/00* | (2006.01) | |
| *A61Q 19/08* | (2006.01) | |

(52) U.S. Cl.
CPC ............ *A61K 36/185* (2013.01); *A61K 8/365* (2013.01); *A61K 8/9789* (2017.08); *A61Q 19/007* (2013.01); *A61Q 19/08* (2013.01); *A61K 2236/15* (2013.01); *A61K 2236/331* (2013.01); *A61K 2236/333* (2013.01); *A61K 2236/51* (2013.01); *A61K 2236/53* (2013.01); *A61K 2800/80* (2013.01)

(58) Field of Classification Search
None
See application file for complete search history.

(56) References Cited

FOREIGN PATENT DOCUMENTS

| CN | 106806161 A | 6/2017 |
| CN | 107308039 A | 11/2017 |

OTHER PUBLICATIONS

Hait et al. (2017) Journal of Medicinal Plants Studies 5(3): 189-192. (Year: 2017).*
Rameshwar et al. (2014) Sch. Acad. J. Pharm 3(2): 100-107 (Year: 2014).*
Zillich et al. (2015) Intern. J. Cosmetic Sci. 37: 455-464. (Year: 2015).*
International Search Report for Application No. PCT/EP2018/086754, dated Apr. 3, 2019, pp. 1-3.
Jain, et al., Assessment of credibility of some folk medicinal claims on *Bombax ceiba* L , Indian Journal of Traditional Knowledge, Jan. 2014, pp. 87-94, vol. 13, No. 1, XP018029848.
John Refaat, et al., Bombacaceae Between the Ethnomedical Uses and Pharmacological Evidences: A Review, The Natural Products Journal, Dec. 2014, pp. 254-270, vol. 4, No. 4, Retrieved from the Internet: https://www.ingentaconnect.com/content/ben/npj/2014/00000004/00000004/art00004 [retrieved on Jul. 26, 2018], XP055495482.
John Refaat, et al., Bombacaceae: A phytochemical review, Pharmaceutical Biology, Sep. 2012, pp. 100-130, vol. 51, No. 1, DOI: 10.3109/13880209.2012.698286, ISSN: 1388-0209, XP055495271.
The Himalaya Drug Company, Acne-n-Pimple Cream, Mar. 2015, Database accession No. 3022367, 4 pages, Retrieved from: GNPD [online], Mintel, XP002783360.
Yi-Gang Yu, Ei Al , In vitro antioxidant activity of Bombax malabaricum flower extracts, Pharmaceutical Biology, Mar. 2011, pp. 569-576, vol. 49, No. 6, DOI: 10.3109/13880209.2010.529614, ISSN: 1388-0209, XP055495281.

* cited by examiner

*Primary Examiner* — Russell G Fiebig
(74) *Attorney, Agent, or Firm* — Lerner, David, Littenberg, Krumholz & Mentlik, LLP (57) ABSTRACT

The invention relates to an extract of flowers, preferably calyxes, from kapok trees, in particular *Bombax costatum*, to a process for preparing same and to the extract obtainable by said process. The invention also relates to a composition comprising such an extract, the composition being advantageously a cosmetic, pharmaceutical or dermatological composition. The invention also relates to such a composition or such an extract for use in preventing or treating disorders or diseases of the skin, the mucous membranes or keratinous appendages and for use in preventing or treating vascular disorders. The invention finally relates to a cosmetic care process for the skin, the keratinous appendages or the mucous membranes, with a view to improving the condition thereof or the appearance thereof, which process consists in administering such a composition or such an extract.

9 Claims, 3 Drawing Sheets

KAPOK TREE FLOWER EXTRACT, AND COSMETIC, PHARMACEUTICAL OR DERMATOLOGICAL COMPOSITIONS CONTAINING SAME

CROSS-REFERENCE TO RELATED APPLICATIONS

The present application is a national phase entry under 35 U.S.C § 371 of International Application No. PCT/EP2018/086754 filed Dec. 21, 2018, which claims priority from French Application No. 1763152 filed Dec. 22, 2017, all of which are hereby incorporated herein by reference.

The invention relates to a composition comprising Kapok tree flower extract, in particular *Bombax costatum* flower extract. The composition is advantageously cosmetic, pharmaceutical or dermatological. The invention also covers a method for the extraction of a Kapok tree flower extract, preferably of a Kapok tree calyxes extract, as well as the extract obtainable by said method. The invention also relates to such a composition or such an extract for its use in the prevention or treatment of disorders or diseases of the skin, mucous membranes or skin appendages, and in the prevention or treatment of vascular disorders. Finally, the invention relates to a cosmetic care method for the skin, skin appendages or mucous membranes, in view of improving their condition or appearance, consisting of administering such a composition or such an extract.

Kapok Tree

The Kapok tree, in particular *Bombax costatum*, is a member of the bombacaceae family (APG: Malvaceae). *Bombax costatum* is also called *Bombax andrieui* or *Bombax houardii*. *Bombax costatum* is more commonly known as the red-flowered silk-cotton tree, cheese-maker tree, red kapok tree, silk cotton tree, Gambia silk-cotton tree, Vaka (in the Moré language) or Boumbou (in the Jula language).

*Bombax* is a pantropical genus comprising 8 species: 2 in Africa, 5 in Asia and 1 in Oceania and is found all the way to the Solomon Islands. In previous times, the *Bombax* genus was much more widely spread. *Bombax costatum* is sometimes regarded as conspecific with *Bombax buonopozense*.

Uses of *Bombax costatum*

Generally, in Africa, *Bombax costatum* is a tree which is a relatively common source of food: the leaves are dried and eaten in the same way as those of Baobab trees and the flowers, in particular the calyxes, are also edible.

The tubercles of the young plants are eaten by cattle.

It has many magical and religious uses as it is sometimes regarded as a sacred tree (Sanou 2013).

In Burkina Faso, the bark is used to stain the teeth red. The flowers are commonly collected for the fleshy calyx which is cooked and eaten as a vegetable. The leaves are also used as a vegetable. The unripe fruit and sometimes the flowers are added as thickeners to sauces. The young, unripe fruit is also used in the preparation of a beverage. The oil of the seeds is edible. The flowers are much appreciated for their melliferous qualities.

Several parts of the tree are used in traditional medicine against various diseases. The root is ground to a powder and eaten as a sauce or applied as a bath against epilepsy. Bark preparations are applied to wounds to promote healing.

In Senegal and Sierra Leone, diuretic properties are attributed to the bark of the stem and root.

The bark is also used to prepare a medication against trichomoniasis, amoebiasis and other forms of dysentery. A bath in an extract of the stem bark is taken against insanity. A powder of the stem bark is used in the composition of a medicine applied by fumigation for headaches. A compress of the stem bark can be applied to the head to treat headaches and toothache.

The leaves are prescribed along with other medicinal plants to treat leucorrhoea and diarrhoea. An extract of the ground leaves is taken as a beverage against problems during birthing. A bath in a ground leaf extract is taken repeatedly to prevent convulsions. An herbal tea made of the dried leaves is drunk or applied to the body to prevent measles. A decoction of the leaves and bark of the stem or root is taken as a beverage for severe oedema. A decoction of the leaves and young shoots is taken to treat jaundice. A leaf decoction is also given as a beverage to children against rickets.

Different parts of the plant are used to promote lactation and as a tonic for fatigue. The skin is rubbed with leaves mixed with shea butter against leprosy.

In Mali, a decoction of the bark and leaves along with parts of other plants is taken for menstrual problems. The leaves are emollient and a warm bath in a leaf decoction may be prescribed for patients with a fever, in particular in children. The leaves are also used as treatment for hookworm and the flowers as treatment for tapeworm.

In Niger, it has been found that the fruit contains 20-25% proteins. The seeds have a high oil content (20%). The fatty acid composition of the oil is as follows: caproic acid 3%, caprylic acid 7%, palmitic acid 8%, stearic acid 3%, oleic acid 49%, linoleic acid 13%, rachidic acid 3%, lignoceric acid 1-2%, and others 13%. The mucilaginous flower extract consists mainly of sugars (rhamnose and arabinose); it constitutes a suitable adhesive for particle panels.

All this data is drawn from an ethnobotanic report by Dr. Lassina SANOU, Water and Forests Director. He works for the Ministry of the Environment and Sustainable Development at the Burkina Faso National Forest Seed Centre (CNRS), based in Ouagadougou (December 2014).

OPCS

The OligoProanthoCyanidins Oligomers, better known as OPCs or procyanidins, are phenol compounds found in many vegetables. The OPCs are polymers of flavonoids, precursors of tannins. The monomers which make up procyanidins are catechin and epicatechin. The procyanidins are therefore made up of the same recurring group, called catechin (formulas Ia and Ib) or epicatechin (formulas IIa and IIb), repeated 2, 3, 4, or 5 times:

(Ia)

(Ib)

(IIa)

(IIb)

Beyond 6 repetitions, the molecules are called Proantho-Cyanidic polymers and have a higher molecular weight. They are very weakly absorbed and, as a result, only have very weak biological activity.

The OPCs are known for their angioprotective properties, as inhibitors of angiotensin converting enzyme, elastase and trypsin, and as providing protection of the vascular walls by binding to the collagen of the connective tissue and by inhibition of collagenase, thus improving the intactness, resistance and elasticity of the walls. They are also known for their antioxidant, anti-free radical, anti-inflammatory and anti-viral properties.

DESCRIPTION OF THE INVENTION

The Applicant has discovered that the flower extracts, preferably the calyxes extract, of the Kapok tree, in particular of *Bombax costatum*, possess cosmetic and dermatological properties that have never been described to date. More particularly, this is the first time that such flower extracts, in particular calyxes extracts, of the Kapok tree, in particular of *Bombax costatum*, have been used as such, for their specific properties.

The object of the invention is a polyphenol-rich extract of Kapok tree flower, preferably of Kapok tree calyxes, the Kapok tree being in particular *Bombax costatum*. Advantageously, the object of the invention is polyphenol-rich extract of *Bombax costatum* flower, preferably of *Bombax costatum* calyxes.

In botany, the flower is the part of the plant comprising, from the outside towards the inside, when it is whole:
- the calyx, consisting of the sepals;
- the corolla, consisting of the petals;
- the androecium, that is to say the stamens (male part) which produce pollen; and
- the gynoecium or pistil, consisting of the carpels (female part).

Within the scope of this invention, the term «flower» includes at least the corolla and calyx. The flower may also be whole.

The extract according to the invention is preferably an extract of Kapok tree calyxes, more advantageously an extract of *Bombax costatum* calyxes.

The term «polyphenol-rich extract» is understood to mean an extract consisting mainly or essentially of polyphenols.

The extract according to the invention advantageously comprises at least 15% by weight of polyphenols, more advantageously at least 20% by weight, relative to the total weight of the dry extract; that is at least 2.5 mg of polyphenols per ml of liquid extract (in gallic acid equivalent). The percentages are given relative to the total weight of said dry extract (before any addition of a drying agent). Advantageously, the extract according to the invention comprises 15% to 40%, more advantageously 20% to 40% by weight of polyphenols relative to the total weight of the dry extract.

Advantageously, the extract according to the invention further comprises at least 10% by weight of OPCS, more advantageously at least 13% by weight, even more advantageously at least 15% by weight, expressed as catechin equivalent, relative to the total weight of said extract, that is to say at least 1.9 mg of OPC per ml of liquid extract. Advantageously, the extract according to the invention comprises from 10% to 25%, more advantageously from 13% to 25%, even more advantageously 15% to 25%, by weight of OPC, expressed as catechin equivalent, relative to the total weight of said dry extract.

Advantageously, the extract according to the invention further comprises at least 6%, advantageously 6% to 10%, by weight of organic acids, in particular alpha-hydroxy acids (AHA), in particular acetic acid, malic acid, lactic acid, citric acid or mixtures thereof, relative to the total weight of the dry extract.

Advantageously, the extract according to the invention further comprises at least 5%, advantageously from 5% to 10%, by weight of flavonoids, expressed as rutin equivalent, relative to the total weight of the dry extract.

According to an advantageous aspect, the extract according to the invention principally comprises (categorised in decreasing order as a function of their content in the extract): polyphenols, OPCS, organic acids and flavonoids.

In particular, such an extract advantageously contains (% molecules of the dry extract obtained and in decreasing order):
- About 20% of polyphenols—in gallic acid equivalent
- About 15% of OPCS (Oligo ProanthoCyanidins—in catechin equivalent),
- About 6% of organic acids (mainly citric and malic acids)
- About 4% of flavonoids (in rutin equivalent).

Within the scope of this invention, the polyphenol-rich extract described above is advantageously obtained by solid/liquid extraction of the Kapok tree flowers, preferably the Kapok tree calyxes, the Kapok tree being in particular *Bombax costatum*, in a solvent chosen from amongst water, ethanol, glycols and mixtures thereof. The extraction solvent is more particularly chosen from amongst binary mixtures of water/glycols, water/ethanol, and mixtures thereof, advantageously in a proportion comprised between 30 and 90%, typically between 50 and 90%, of glycol and/or ethanol in water. In particular, the extraction solvent is chosen from amongst binary mixtures of water/propanediol, water/propylene glycol and water/ethanol, in particular water/propanediol, more particularly water/1,3-propanediol.

More advantageously, the polyphenol-rich extract described above is obtained by solid/liquid extraction of the Kapok tree flowers, preferably the Kapok tree calyxes, the Kapok tree being in particular *Bombax costatum*, in a solvent chosen from amongst water, glycols and mixtures thereof. The extraction solvent is more particularly chosen from amongst binary mixtures of water/glycol, advantageously in a proportion comprised between 30 and 90%, typically between 50 and 90%, of glycol in water. In particular, the extraction solvent is chosen from amongst binary mixtures of water/propanediol and water/propylene glycol, in particular water/propanediol, more particularly water/1,3-propanediol.

Advantageously, the above-mentioned glycols are glycols of plant origin, in particular propanediol and/or propylene glycol, more particularly propanediol, in particular 1,3-propanediol.

In a more advantageous manner, the polyphenol-rich extract described above is obtained by solid/liquid extraction of the flowers, preferably the calyxes, of the Kapok tree, in particular of *Bombax costatum*, in a binary mixture of water/1,3-propanediol, advantageously in a proportion comprised between 30 and 90%, typically between 50 and 90%, of 1,3-propanediol in water. This particular solvent results in better yields of the desired active ingredients, in particular polyphenols, OPCS, flavonoids and/or organic acids.

In an advantageous manner, when solid/liquid extraction of the flowers, preferably the calyxes, of the Kapok tree, in particular of *Bombax costatum*, is carried out in a binary mixture of water/solvent, the proportions of the solvent in water are between 50 and 90%.

An object of the invention is also a method for the preparation of a polyphenol-rich extract of Kapok tree flower, preferably of Kapok tree calyxes, the Kapok tree being in particular *Bombax costatum*, advantageously of *Bombax costatum* calyxes, comprising at least one solid/liquid extraction step in an appropriate solvent or a solvent mixture and under optimum pH, duration and temperature, known to the person skilled in the art.

Advantageously according to the invention, the method for preparation of a polyphenol-rich extract of Kapok tree flower, preferably of Kapok tree calyxes, the Kapok tree being in particular *Bombax costatum*, comprises the following successive steps:
  a) grinding the flowers, in particular the calyxes;
  b) extracting the ground flowers, in particular the ground calyxes, in an appropriate solvent or a solvent mixture and under optimum pH, duration and temperature conditions;
  c) separating the solid phase and the liquid phase by decantation and/or centrifugation and/or successive filtration; and
  d) if necessary, drying the extract obtained in step c).

The plant grinding step a) can be carried out using methods known to the person skilled in the art, in particular with the aid of a knife mill, hammer mill, etc.

In step b), the extraction phase is preferably carried out in the presence of water and/or glycols and/or ethanol alone or in a binary mixture. Advantageously, the extraction solvent used in step b) is chosen from amongst binary mixtures of water/glycols, water/ethanol, and mixtures thereof, advantageously in a proportion comprised between 30 and 90%, typically between 50 and 90%, of glycol and/or ethanol in water. In particular, the extraction solvent is chosen from amongst binary mixtures of water/propanediol, water/propylene glycol and water/ethanol, in particular water/propanediol, more particularly water/1,3-propanediol. More advantageously, the extraction solvent used in step b) is chosen from amongst binary mixtures of water/glycols, advantageously in a proportion comprised between 30 and 90%, typically between 50 and 90%, of glycol in water. In particular, the extraction solvent is chosen from amongst binary mixtures of water/propanediol, water/propylene glycol, in particular water/propanediol, more particularly water/1,3-propanediol.

Advantageously, the above-mentioned glycols are glycols of plant origin, in particular propanediol and/or propylene glycol, more particularly propanediol, in particular 1,3-propanediol.

In a more advantageous manner, the extraction solvent used in step b) is a binary mixture of water/1,3-propanediol, advantageously in a proportion comprised between 30 and 90%, typically between 50 and 90%, of 1,3-propanediol in water. This particular solvent results in better yields of the desired active ingredients, in particular polyphenols, OPCS, flavonoids and/or organic acids.

In an advantageous manner, when solid/liquid extraction of the flowers, preferably the calyxes, of the Kapok tree, in particular of *Bombax costatum*, is carried out in a binary mixture of water/solvent, the proportions of the solvent in water are between 50 and 90%.

Moreover, step b) of the solid/liquid extraction is preferably carried out at a temperature between 20° C. and 90° C., in particular between 30° C. and 80° C., more particularly between 30° C. and 75° C., typically 50° C.

The duration of extraction is advantageously between 30 minutes and 4 hours, in particular between 1 hour and 3 hours, advantageously it is about 2 hours.

Step c) of separating the solid phase from the liquid phase is carried out using methods known to the person skilled in the art, in particular by decantation, centrifugation and/or successive filtration, preferably by filtration. Step c) is carried out until absolute transparency and microbiological hygiene is achieved.

Advantageously, the polyphenol-rich extract according to the invention can be stabilised by the drying step d) by means of methods known to the person skilled in the art.

The drying step d) can for example be carried out in the presence of a support of the maltodextrin or acacia fibre type (Fibregum® supplied by CNI), for example. The support content varies according to a ratio ranging from 0% to 80% of the support relative to the percentage of dry material obtained in the liquid form of the extract.

The extract is preferably dried by freeze drying or atomization in order to obtain the final powder. The final powder advantageously comprises 30 to 70% by weight of dry extract material, the complement at 100% being the freeze-drying or atomisation support. More advantageously, the final powder comprises 50% of dry material originating from the extract and 50% of the freeze-dried or atomization support.

According to another advantageous embodiment, the extract according to the invention can be stabilized physically and microbiologically by a solvent chosen from amongst glycols, such as propanediol, typically 1,3-propanediol, said solvent being present in a proportion adapted to such stabilisation. Preferably, the glycol, in particular propanediol, preferably 1,3-propanediol, will be present alone or in combination with water in a proportion in the range between 30 to 90% and preferably between 50 and 90% of glycol in water.

Thus, this invention further relates to another composition comprising a polyphenol-rich extract of Kapok tree flower, preferably of Kapok tree calyxes, the Kapok tree being in particular *Bombax costatum*, according to the invention, a solvent chosen from amongst the glycols, such as propanediol, in particular 1,3-propanediol, in an effective quantity for a physical and microbiological stabilizing action, in water if need be. The effective quantities for a physical and microbiological stabilizing action are advantageously those described above.

Preferably, as an example, the polyphenol-rich extract according to the invention can be obtained according to the following method:

a') Putting the ground flower in solution at 5% (w/w) in a mixture of 1,3-propanediol/water (60/40);
b') Extraction with stirring for 2 h at 40° C.;
c') Purification by successive filtrations steps; and
d') Sterile filtration.

In the description which follows, the term «extract according to the invention» designates the extract as such, as defined above, or the extract that can be obtained by the method of the invention as described above. The extract that can be obtained by the method of the invention as described above presents the same composition as the extract according to the invention as such, as defined above.

Another object of the invention is a composition comprising a polyphenol-rich extract of Kapok tree flower, preferably of Kapok tree calyxes, the Kapok tree being in particular *Bombax costatum*, according to the invention, as an active ingredient, and an appropriate excipient where necessary. The extract according to the invention is as defined in the paragraphs above concerning the extract as such and those concerning the extract that can be obtained by the method of the invention.

The composition is advantageously cosmetic, pharmaceutical or dermatological. Said composition is preferably formulated for administration by external topical route.

Advantageously, the composition according to the invention comprises from 0.001 to 10%, typically from 0.01% to 5% by weight of the extract according to the invention, the extract weight being expressed as the dry extract, relative to the total weight of the composition.

The composition according to the invention can further include one or more active ingredients.

The composition according to the invention can be formulated in the form of different preparations adapted to topical administration and includes creams, emulsions, milks, ointments, lotions, oils, aqueous, alcoholic or glycolic solutions, powders, patches, sprays, shampoos, varnishes or any other product for external application.

Depending on its type (cosmetic, pharmaceutical or dermatological), the composition according to the invention can further include at least one cosmetically, pharmaceutically or dermatologically acceptable excipient. In particular, the composition according to this invention can further include at least one adjuvant that is cosmetically, pharmaceutically or dermatologically known to the person skilled in the art, chosen from amongst surfactants, thickeners, preservatives, perfumes, dyes, chemical or mineral filters, hydrating agents, thermal waters, etc. The person skilled in the art knows how to adapt formulation of the composition according to the invention by using his or her general knowledge.

The dosages and optimum galenic formulations according to the invention can be established according to the criteria usually taken into account when formulating a pharmacological, dermatological or cosmetic treatment suited to a patient or an animal, such as for example the age and body weight of the patient or animal, severity of the general condition, tolerance of treatment, side effects observed, skin type.

An object of the invention is also an extract according to the invention or a composition according to the invention for its use in the prevention and/or treatment of disorders or diseases of the skin and/or mucous membranes (gums, periodontium, genital mucosa) and/or skin appendages (hair and nails), whether immature, normal or mature/elderly, advantageously the inflammatory reactions, oxidation reactions, disorders related to radical attacks whether linked to pollution or not, barrier or homeostasis disorders, aging, in particular chronological aging and/or actinic aging, and/or mechanical or thermal aggressive factors, more advantageously inflammatory and irritative reactions or diseases, or barrier or homeostasis disorders of the skin, skin appendages and/or mucous membranes (gums, periodontium, genital mucosa), whether immature, normal or mature/elderly.

An object of the invention is also an extract according to the invention for its use in the prevention and/or treatment of vascular disorders, in particular redness and blotchiness.

Another object of the invention is also the use of an extract according to the invention or a composition according to the invention to produce a cosmetic, pharmaceutical or dermatological composition to prevent and/or treat disorders or diseases of the skin and/or mucous membranes (gums, periodontium, genital mucosa) and/or skin appendages (hair and nails), whether immature, normal or mature/elderly, advantageously the inflammatory reactions, oxidation reactions, disorders related to radical attacks whether linked to pollution or not, barrier or homeostasis disorders, aging, in particular chronological aging and/or actinic aging, and/or mechanical or thermal aggressive factors, more advantageously inflammatory and irritative reactions or diseases, or barrier or homeostasis disorders of the skin, skin appendages and/or mucous membranes (gums, periodontium, genital mucosa), whether immature, normal or mature/elderly.

An object of the invention is also an extract according to the invention or a composition according to the invention for manufacturing a cosmetic, pharmaceutical or dermatological composition to prevent and/or treat vascular disorders, in particular redness and blotchiness.

Moreover, an object of the invention is also a method for preventing and/or treating disorders or diseases of the skin and/or mucous membranes (gums, periodontium, genital mucosa) and/or skin appendages (hair and nails), whether immature, normal or mature/elderly, advantageously the inflammatory reactions; oxidation reactions, disorders related to radical attacks whether linked to pollution or not; barrier or homeostasis disorders; aging, in particular chronological aging and/or actinic aging; and/or mechanical or thermal aggressive factors, more advantageously inflammatory and irritative reactions or diseases, or barrier or homeostasis disorders of the skin, skin appendages (hair and nails) and/or mucous membranes (gums, periodontium, genital mucosa), whether immature, normal or mature/elderly, comprising the administration, in particular topical administration, of an effective amount of an extract according to the invention or composition according to the invention, to a subject in need thereof.

An object of the invention is also a method for preventing and/or treating vascular disorders, in particular redness and blotchiness, comprising administering, in particular topically administering, of an effective amount of an extract according to the invention or composition according to the invention, to a subject in need thereof.

In particular, the composition or extract according to the invention is intended for the prevention and/or treatment of inflammatory reactions or irritative reactions or diseases, or barrier or homeostasis disorders of the skin, skin appendages (hair and nails) and/or mucous membranes (gums, periodontium, genital mucosa), whether immature, normal or mature/elderly.

Advantageously, the inflammatory or irritative reactions, disorders or diseases or the barrier or homeostasis disorders of the skin are: acne, rosacea or erythrocouperose, vascular disorders, in particular redness and blotchiness, seat dermatitis, atopic dermatitis, eczema, contact dermatitis, irritative dermatitis, allergic dermatitis, seborrheic dermatitis (cradle cap), sensitive skin, reactive skin, dry skin (xerosis), dehydrated skin, skin with redness, cutaneous erythema, elderly or photo-aged skin, photosensitive skin, pigmented skin (melasma, post inflammatory pigmentation, etc.), skin with stretch marks, sunburn, irritation by chemical, physical (for example, natural tissue tension in pregnant women), bacteriological and fungal agents, cutaneous aging, in particular photo-aging and disorders related to radical attacks linked to chemical or atmospheric pollution, and/or linked to exposure to UV or IR.

Advantageously, the inflammatory or irritative reactions, disorders or diseases, or barrier or homeostasis disorders of the mucous membranes are gingivitis (sensitive gums in new-born babies, hygiene problems due to smoking or other) and irritation of the internal or external male or female genital areas.

Advantageously, the inflammatory or irritative reactions, disorders or diseases, or barrier or homeostasis disorders of the skin appendages are brittle nails, fragile nails, damaged hair, brittle hair, dry hair, alopecia, seborrheic dermatitis and follicular dermatitis.

In a particularly advantageous manner, the composition or extract according to the invention is intended to be anti-aging, against cutaneous aging, in particular chronological aging or actinic aging, for example related to exposure to the sun or to inflammatory phenomena, or even to act in irritated skin.

An object of the invention is also the cosmetic use of an extract according to the invention in the treatment and/or prevention of dehydrated skin; skin with redness; elderly or photo-aged skin; photosensitive skin; cutaneous aging, in particular photo-aging; and disorders related to radical attacks linked to chemical or atmospheric pollution, and/or linked to exposure to UV or IR.

An object of the invention is also the cosmetic use of an extract according to the invention or a composition according to the invention for the treatment of skin appendages, in particular for the treatment and/or prevention of brittle nails; fragile nails; damaged hair; brittle hair; and dry hair.

The invention also relates to a cosmetic care method for skin and/or skin appendages and/or mucous membranes, in view of improving their condition and/or appearance, consisting of administering a composition or an extract according to this invention.

In particular, the invention relates to a cosmetic care method for skin and/or skin appendages, in view of preventing changes in the skin barrier and its dehydration, consisting of application to the skin and/or skin appendages of a composition or an extract according to this invention.

The invention relates to a cosmetic care method for skin and/or skin appendages, in view of preventing aging consisting of application to the skin and/or skin appendages of a composition or an extract according to this invention.

The invention also relates to the cosmetic use of a composition or an extract according to the invention to hydrate the skin and/or mucous membranes, to act on skin elasticity or firmness, in particular as a firming or anti-wrinkle agent, to act on sensitive skin, or to act against pollution.

The following examples help to illustrate the invention.

EXAMPLE 1: EXTRACTS ACCORDING TO THE INVENTION

Polyphenol-rich extracts of *Bombax costatum* calyxes are obtained according to the following method:
a) ground *Bombax costatum* calyxes are put in solution in a mixture of water/propanediol 30/70, 20/80 or 10/90 w/w
b) extraction 2 h at 50° C.
c) solid/liquid separation by successive filtrations.

The polyphenol-rich liquid extract obtained in this way has the following characteristics (% by weight of molecules/dry extract of the extract obtained):

| Mixture of water/propanediol (w/w) | 30/70 | 20/80 | 10/90 |
|---|---|---|---|
| Dry extract(2 h, 105° C., ventilated oven) | 1.6% | 1.2% | 1.3% |
| Total polyphenols (eq. Gallic acid) | 19% | 23% | 22% |
| OPC (eq. Catechin) | 20.6% | 22.5% | 24% |
| Flavonoids (eq. Rutin) | 4.6% | 6% | 5% |
| Antioxidant activity (DPPH) | 31 (µg) | 12 (µg) | 27(µg) |

The Kapok tree extract according to the invention obtained according to example 1 (20/80) is also referred to as KPO extract in the text and Figures.

EXAMPLE 2: EXTRACT ACCORDING TO THE INVENTION

A polyphenol-rich extract of *Bombax costatum* calyxes is obtained according to the following method:
a) ground *Bombax costatum* calyxes are put in solution in a mixture of water/ethanol 20/70 w/w;
b) extraction 2 h at 75° C.; and
c) solid/liquid separation by successive filtrations.

The polyphenol-rich liquid extract obtained in this way has the following characteristics (% molecules/dry extract of the extract obtained):

| | |
|---|---|
| Dry extract (2 h, 105° C., ventilated oven) | 1.05% |
| Total polyphenols (eq. Gallic acid) | 24% |
| OPC (eq. Catechin) | 14% |
| Flavonoids (eq. Rutin) | 7.8% |
| Antioxidant activity (DPPH) | 34 (µg) |

EXAMPLE 3: BIOLOGICAL ACTIVITY TESTS OF THE EXTRACT ACCORDING TO THE INVENTION

In the example below, the extract tested, called KPO extract, is an extract according to the invention obtained according to example 1 (mixture of water/propanediol 20/80).

1—Screening of Gene Expression in Fibroblast, Keratinocyte and Skin Explant Cultures The effect of KPO extract on messenger RNA expression characteristic of cosmetic requirements was evaluated in characteristic skin models: normal human epidermal keratinocytes or normal human dermal fibroblasts were incubated for 24 hours with 0.0005% and 0.001% KPO extract (dry extract concentration: d.e.). Additionally, skin explants were incubated for 24 h with 0.005% and 0.001% KPO extract (d.e.). At the end of incubation, the mRNA was extracted and the expression of 90 genes of interest was analysed by RT-qPCR.

The results showed potential biological activity of the KPO extract in the following areas:

Neosynthesis, structuring and remodelling of the dermal matrix: stimulation of DCN, SPARC, BGN, COL3A1, TP63, TGFB1 genes;

Adhesion and barrier function: stimulation of CD44, CTNNA1, ITGA2, SDC1, LAMC2, TNC, COL17A1, VCAN, PXN, LAMA5, S100A7 genes;

Longevity and renewal: stimulation of SIRT6, ATP5A1, INSR, EGF, SIRT3 genes;

Pigmentation: stimulation of POMC and PMEL genes;

Detoxification and antioxidant defence: stimulation of BSG, CAT, GLRX, MSRA, MSRB2, TXN, SOD2, PPIA, HMOX1, HSPB1, DGAT1, GBA genes.

To summarize, two main effects of the KPO extract emerge from this analysis. The first is adhesion and the barrier function with strong expression of the genes involved in cell-cell or cell-matrix adhesion. This activity is boosted by extracellular matrix neosynthesis and structuring activities which show an effect on tissue firmness. The stress response is also very much present with the induction of many genes some of which show in particular strong induction. In this stress response, protection against oxidative stress is predominant. Reaction pathways to other types of stress and detoxification pathways are also activated.

2—Gene Expression of Markers of the Dermal Extracellular Matrix and of Cell Communication The effect of the KPO extract was evaluated on the gene expression of markers involved in cell communication and in the organisation of the dermal extracellular matrix in the fibroblasts: normal human dermal fibroblasts were incubated for 6 hours or 24 hours with 0.0005% or 0.001% KPO extract (d.e.) or TGFβ1 at 5 ng/ml (positive control for dermal matrix induction markers). At the end of incubation, the gene expression of the following markers was analysed by RT-qPCR.

CTNNA1 (Catenin α): binds to cadherins to promote cellular interactions.

Syndecan: proteoglycan which consolidates cell/cell and cell/matrix interactions.

Laminin 5 (α3β3γ2): a molecule that assists adhesion to the basal membrane.

TNC (Tenacin C): extracellular matrix proteins involved in cohesion of the dermo-epidermal junction and which promote the synthesis of collagen VII.

SPARC: protein associated with various constituents of the extracellular matrix and which contributes to its organisation.

BGN (Biglycan): proteoglycan involved in the assembly of collagen fibres.

Versican: a major component of the ECM which plays a central role in the morphogenesis and maintenance of tissues. It also contributes to the formation of the elastic fibres of the skin.

The collagens which give the dermis its firmness and resistance to pressure qualities, representing around 70% of the dermal Extra Cellular Matrix (ECM) components, the majority being of type I collagen (85-90% of dermal collagen) which is frequently associated with type III collagen.

Type IV and VII collagen: glycoproteins, constituents of the Dermo-Epidermal Junction.

Fibronectin: is a high-molecular weight glycoprotein. It plays a role in the structure of the dermal ECM.

The elastic fibres are responsible for skin elasticity. They result from the assembly of two major components: elastin (1 to 3% of the dermis) and the microfibrils.

LOXL: responsible for the assembly of elastin fibres.

Decorin: proteoglycan involved in the assembly of the matrix.

Dermatopontin: plays a role in the assembly of collagen fibres; it is important for maintaining the structural arrangement of the dermal extracellular matrix and tissue flexibility.

Laminin 5 (α3β3): a molecule that assists adhesion to the basal membrane (Dermo-Epidermal Junction).

The results are given as relative quantities (RQ) with respect to the untreated control. The significance of the results was evaluated using a statistical test (one-factor variance analysis followed by a Dunnet test): *$p<0.05$; $p<0.01$; *$p<0.001$; ns: non-significant $p>0.05$.

The results are grouped together in tables 1 and 2 below. They show a considerable inductive effect of the KPO extract on the set of markers studied, suggesting a strong efficacy potential in structuration of the dermal matrix, Dermo-Epidermal Junction (DEJ) and the cell communication method. The KPO extract thus plays a role in hydration, elasticity, dermal exchanges (EDJ) and skin aging.

TABLE 1

Analysis of gene expression after 6 h of treatment:

| Gene evaluated | Negative Control | Positive Control (TGFβ1 5 ng/ml) | KPO 0.0005% | KPO 0.001% |
|---|---|---|---|---|
| SPARC | 1.00 | 1.28 ns | 1.37 *** | 1.60 ** |
| BGN | 1.00 | 1.28 ns | 1.73 ** | 2.11 *** |
| CTNNA1 | 1.00 | 1.07 ns | 1.48 * | 1.48 *** |
| Syndecan | 1.00 | 1.85 ns | 1.41 ns | 1.73 ns |
| TNC | 1.00 | 0.94 ns | 1.41 ns | 1.73 * |
| Versican | 1.00 | 1.61 ns | 1.15 ns | 1.24 ns |
| Collagen I | 1.00 | 0.84 ns | 1.33 ns | 2.08 *** |
| Collagen III | 1.00 | 0.91 ns | 1.24 * | 1.96 *** |
| Collagen IV | 1.00 | 1.68 *** | 1.33 ns | 1.55 ** |
| Collagen VII | 1.00 | 1.96 *** | 0.86 ns | 1.41 * |
| Fibronectin | 1.00 | 1.09 ns | 1.22 ns | 1.60 ** |
| Elastin | 1.00 | 0.72 ns | 1.26 ns | 1.96 *** |
| LOXL | 1.00 | 1.05 ns | 1.46 ** | 1.99 ** |
| Decorin | 1.00 | n.d. | 1.29 * | 1.30 * |
| Dermatopontin | 1.00 | 1.14 ns | 1.32 * | 1.49 * |
| Laminin 5α3 | 1.00 | n.d. | 2.17 * | 1.64 ns |
| Laminin 5β3 | 1.00 | n.d. | 1.48 * | 1.61 * |

TABLE 2

Analysis of gene expression after 24 h of treatment:

| Gene evaluated | Negative Control | Positive Control (TGFβ1 5 ng/ml) | KPO 0.0005% | KPO 0.001% |
|---|---|---|---|---|
| SPARC | 1.00 | 2.00 *** | 1.65 *** | 2.12*** |
| BGN | 1.00 | 2.92 *** | 2.05 *** | 2.61 ** |
| CTNNA1 | 1.00 | 1.07 ns | 1.47 * | 1.80 ** |

TABLE 2-continued

Analysis of gene expression after 24 h of treatment:

Degree of expression (Relative Quantity)

| Gene evaluated | Negative Control | Positive Control (TGFβ1 5 ng/ml) | KPO 0.0005% | KPO 0.001% |
|---|---|---|---|---|
| Syndecan | 1.00 | 8.08 *** | 1.98 * | 2.65 * |
| TNC | 1.00 | 1.79 * | 1.53 ns | 1.72 * |
| Versican | 1.00 | 2.87 ** | 1.45 ** | 1.06 ns |
| Collagen I | 1.00 | 2.30 * | 2.31 * | 4.91 *** |
| Collagen III | 1.00 | 1.24 ns | 1.35 ns | 3.16 *** |
| Collagen IV | 1.00 | 2.81 ** | 1.60 ** | 2.08 *** |
| Collagen VII | 1.00 | 3.07 *** | 1.20 ns | 1.78 ns |
| Fibronectin | 1.00 | 2.12 * | 1.27 ns | 1.77 *** |
| Elastin | 1.00 | 3.65 ** | 2.50 * | 6.20 *** |
| LOXL | 1.00 | 1.10 ns | 1.39 * | 2.28 *** |
| Decorin | 1.00 | n.d. | 1.19 *** | 1.58 * |
| Dermatopontin | 1.00 | 1.36 * | 1.41 * | 2.00*** |
| Laminin 5α3 | 1.00 | n.d. | 1.58 * | 1.60 * |
| Laminin 5β3 | 1.00 | n.d. | 1.35 ns | 1.68 * |

3—Evaluation of Anti-Protease Activity in Dermal Fibroblasts

The KPO extract was evaluated for its capacity to limit the production of MMP1 (Matrix MetalloProteinase-1) triggered by inflammatory stress in the dermal fibroblasts. Normal human dermal fibroblasts were pre-incubated for 24 hours with KPO at 0.0005% or 0.001% (d.e.). The fibroblasts were then stimulated by 100 nM of PMA (Phorbol Myristate Acetate) and incubated overnight with KPO extract. The production of MMP1 was evaluated by ELISA assay in cell supernatants. The results are given in pg of MMP1 per mg of total proteins (determined by BC Assay). The significance was evaluated by means of one-factor variance analysis followed by a Tukey test: *$p<0.05$; ***$p<0.001$; ns: non-significant $p>0.05$.

The results are grouped together in table 3 below. The KPO extract significantly inhibited MMP1 release triggered by PMA stress in the fibroblasts; this result shows a protective effect of the dermal matrix and this a chronological and actinic anti-aging effect.

TABLE 3

Production of MMP1 in fibroblasts stimulated by PMA:

| | MMP1 (pg/mg of proteins) | |
|---|---|---|
| Control | 3.859 ± 0.623 | |
| PMA | 11.358 ± 2.560 | +194% vs control *** |
| KPO at 0.0005% | 8.230 ± 0.768 | −28% vs PMA (ns) |
| KPO at 0.001% | 7.727 ± 0.770 | −32% vs PMA * |

4—Evaluation of Anti-Inflammatory Potential

The anti-inflammatory activity of the KPO extract was evaluated in keratinocytes stimulated by PMA treatment.

Normal human epidermal keratinocytes were pre-incubated for 24 hours with KPO extract at 0.001%, 0.002% or 0.005% (d.e.) or reference anti-inflammatory molecules dexamethasone at 0.1 μM or indomethacin at 0.1 μM. The keratinocytes were then stimulated by 10 μg/ml of PMA (Phorbol Myristate Acetate) and incubated overnight with KPO extract or reference molecules. The production of inflammatory mediators Interleukin-8 (IL*), Interleukin-1β (IL1β) and Prostaglandin E2 (PGE2) was evaluated by ELISA assay in cell supernatants. The significance was evaluated by means of one-factor variance analysis followed by a Tukey test: *$p<0.05$; ***$p<0.001$; ns: non-significant $p>0.05$.

The results are grouped together in tables 4, 5 and 6 below. The KPO extract significantly inhibited the release of cytokines IL1β and IL8, and to a lesser degree PGE2, triggered by pro-inflammatory stress in the keratinocytes. These results show the anti-inflammatory potential of the KPO extract and an anti-aging effect on sensitive skin, or even on irritated skin.

TABLE 4

Production of IL8 in keratinocytes stimulated by PMA:

IL8 (pg/ml)/OD neutral red

| | Mean | Standard deviation | |
|---|---|---|---|
| Control | 47.215 | 4.711 | |
| PMA | 1420.626 | 92.557 | +2909% vs Control *** |
| KPO at 0.001% | 1198.008 | 154.124 | −16% vs PMA * |
| KPO at 0.002% | 795.287 | 84.255 | −44% vs PMA *** |
| KPO at 0.005% | 338.854 | 18.731 | −76% vs PMA *** |

TABLE 5

Production of IL1β in keratinocytes stimulated by PMA:

IL1Beta (pg/ml)/OD neutral red

| | Mean | Standard deviation | |
|---|---|---|---|
| Control | 0.007 | 0.000 | |
| PMA | 0.040 | 0.006 | +451% vs Control *** |
| Dexa + PMA | 0.026 | 0.002 | −35% vs PMA ** |
| KPO at 0.001% | 0.018 | 0.003 | −55% vs PMA *** |
| KPO at 0.002% | 0.017 | 0.003 | −57% vs PMA *** |
| KPO at 0.005% | 0.017 | 0.003 | −57% vs PMA *** |

TABLE 6

Production of PGE2 in keratinocytes stimulated PMA:

PGE2 (pg/ml)/OD neutral red

| | Mean | Standard deviation | |
|---|---|---|---|
| Control | 220.878 | 18.449 | |
| PMA | 802.843 | 75.214 | +263% vs Control *** |
| Dexa + PMA | 617.645 | 61.477 | −23% vs PMA ** |
| Indo + PMA | 181.780 | 15.506 | −77% vs PMA *** |
| KPO at 0.001% | 631.360 | 24.516 | −21% vs PMA * |
| KPO at 0.002% | 701.909 | 60.353 | −13% vs PMA (ns) |
| KPO at 0.005% | 735.274 | 60.135 | −8% vs PMA (ns) |

5—Evaluation of Antioxidant Potential

The antioxidant potential of the KPO extract was evaluated in an assay model of intracellular ROS (Reactive Oxygen Species) induced by pro-oxidising $H_2O_2$ stress. Normal human epidermal keratinocytes were pre-incubated for 24 hours with KPO extract at 0.001%, 0.002% or 0.005% (d.e.) or reference anti-inflammatory molecules Quercetin at 10 μM or Vitamin C at 500 μM. The cell layer was then contacted with a DCFH-DA probe prior to induction of oxidative stress by 100 μM of $H_2O_2$. The amount of ROS produced was evaluated by measuring the fluorescence emitted when the probe is oxidised. The results were analysed statistically by one-factor variance analysis followed by a Tukey test: $p<0.01$; *$p<0.001$.

The results are grouped together in table 7 below. The KPO extract significantly inhibited the production of ROS triggered by the presence of $H_2O_2$. These results demonstrate a powerful antioxidant potential. The KPO extract can therefore be advantageously used against pollution and aging.

TABLE 7

Production of ROS in keratinocytes subjected to $H_2O_2$ stress:

| | ROS (Arbitrary Unit) | |
|---|---|---|
| | Mean | Standard deviation |
| Control | 18564.862 | 12917.522 |
| $H_2O_2$ at 100 μM | 133342.523 | 52149.942 +618% vs control *** |
| Quercetin at 10 μmol/l | 12959.361 | 2587.250 −90% vs $H_2O_2$ *** |
| Vit C 500 μM | 12807.703 | 4220.635 −90% vs $H_2O_2$ *** |
| KPO at 0.001% | 68750.713 | 10417.179 −48% vs $H_2O_2$ ** |
| KPO at 0.002% | 59761.384 | 15339.601 −55% vs $H_2O_2$ *** |
| KPO at 0.005% | 26779.475 | 6550.110 −80% vs $H_2O_2$ *** |

6—In Vitro Evaluation of an Anti-Wrinkle and Firming Effect

The «firming» effect of KPO extract was evaluated in a GlasBox® system on fibroblasts from the base of a wrinkle and on fibroblasts from adjacent non-wrinkled skin («healthy» fibroblasts). The GlasBox® system makes it possible to measure, within a dermal equivalent, the contractile force developed by the fibroblasts. Fibroblasts originating from the base of a wrinkle have less contraction force than those from adjacent non-wrinkled skin and in this way it is possible to evaluate the «anti-wrinkle» effect of a compound.

Dermal equivalents were prepared by mixing fibroblasts (healthy skin or wrinkled skin) with a collagen solution. The fibroblasts originated from a sample obtained from the same patient (65-year-old woman) from the depth of the wrinkle, on the one hand, and from a nearby non-wrinkled skin. This mixture was cooled in rectangular GlasBox® tanks. A medium containing or not containing KPO extract at 0.005% or 0.001% (d.e.) was added.

Two flexible silicon blades were introduced into each of these tanks. The dermal equivalent therefore develops between two blades equipped with a strain gauge («sensor»). Under the effect of the retraction force developed by the fibroblasts, the silicon blades are deformed; this is seen by a variation in the electrical resistance value of the strain gauge. This variation, measured in real time, is representative of the force developed within the dermal equivalent. The isometric forces were thus measured for 24 hours.

Figure 1:
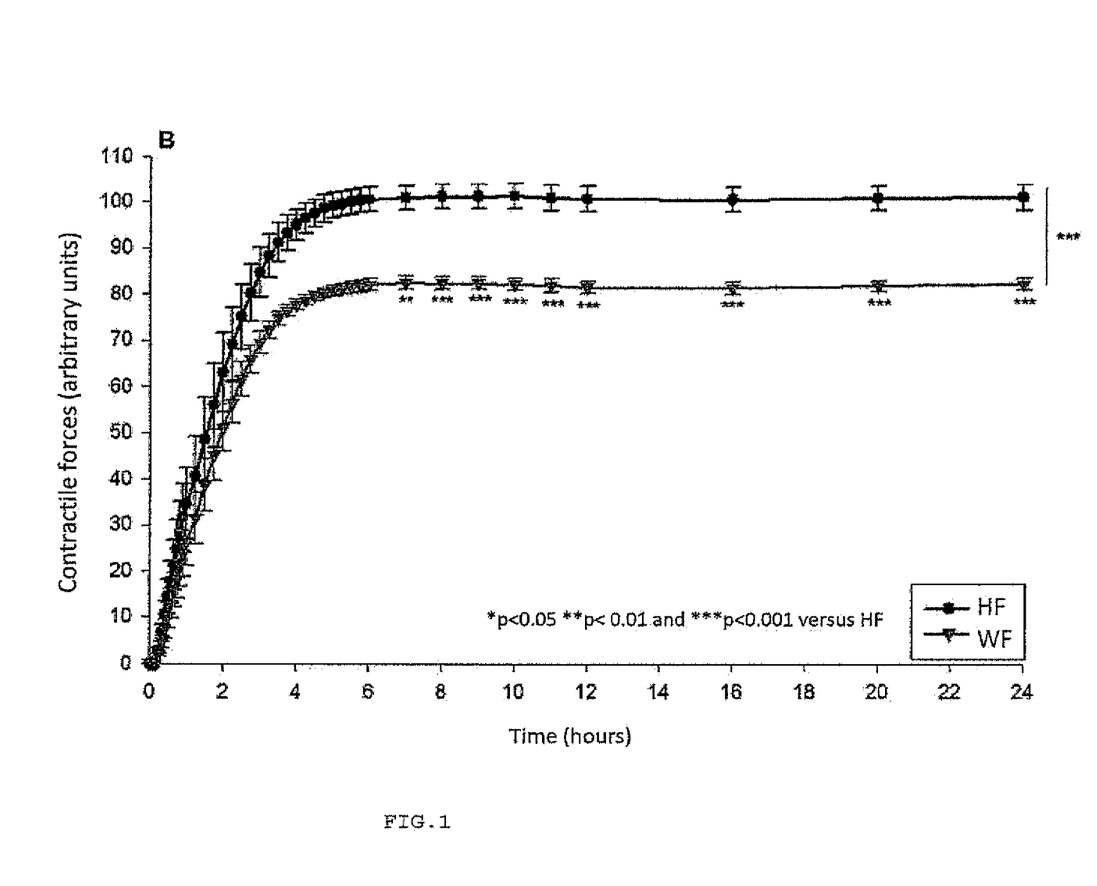
FIG. 1 represents the contractile forces developed by wrinkle fibroblasts (WF) compared to healthy fibroblasts (HF).
Figure 2:
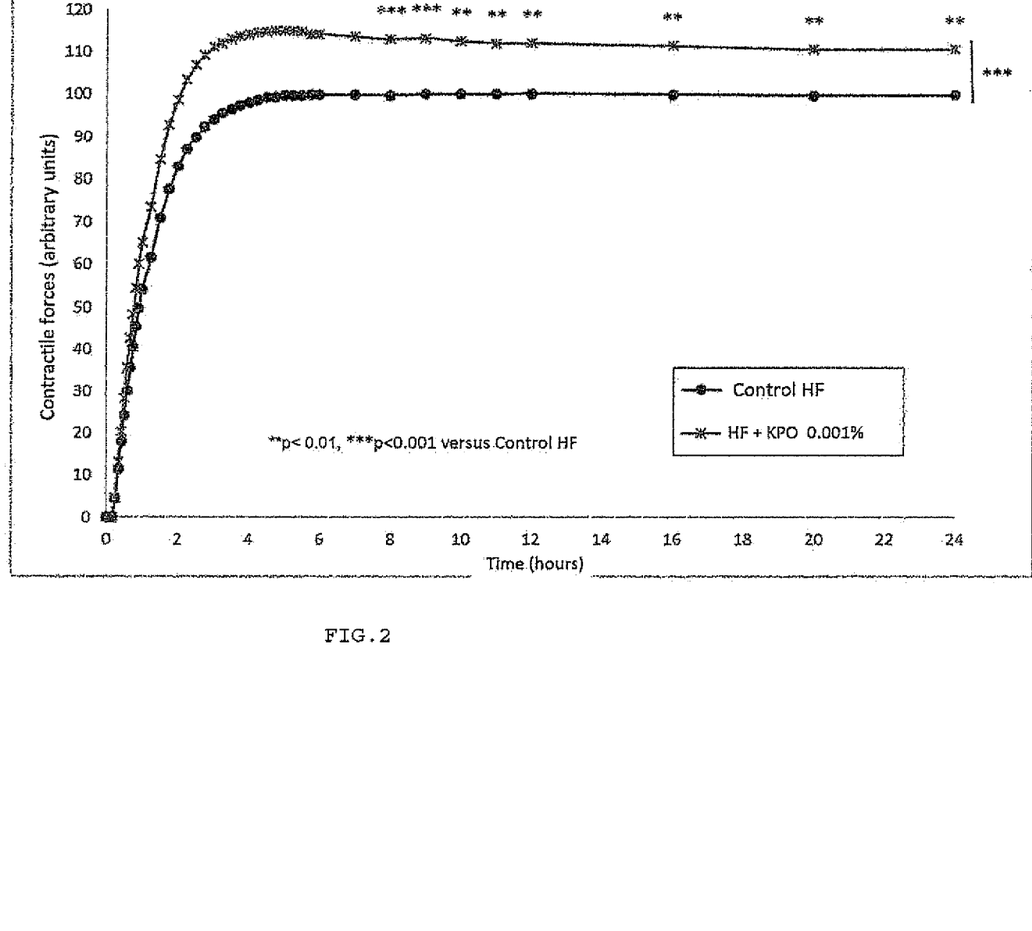
FIG. 2 represents the contractile forces developed by healthy fibroblasts (HF) in the presence or not of the KPO extract according to the invention.
Figure 3:
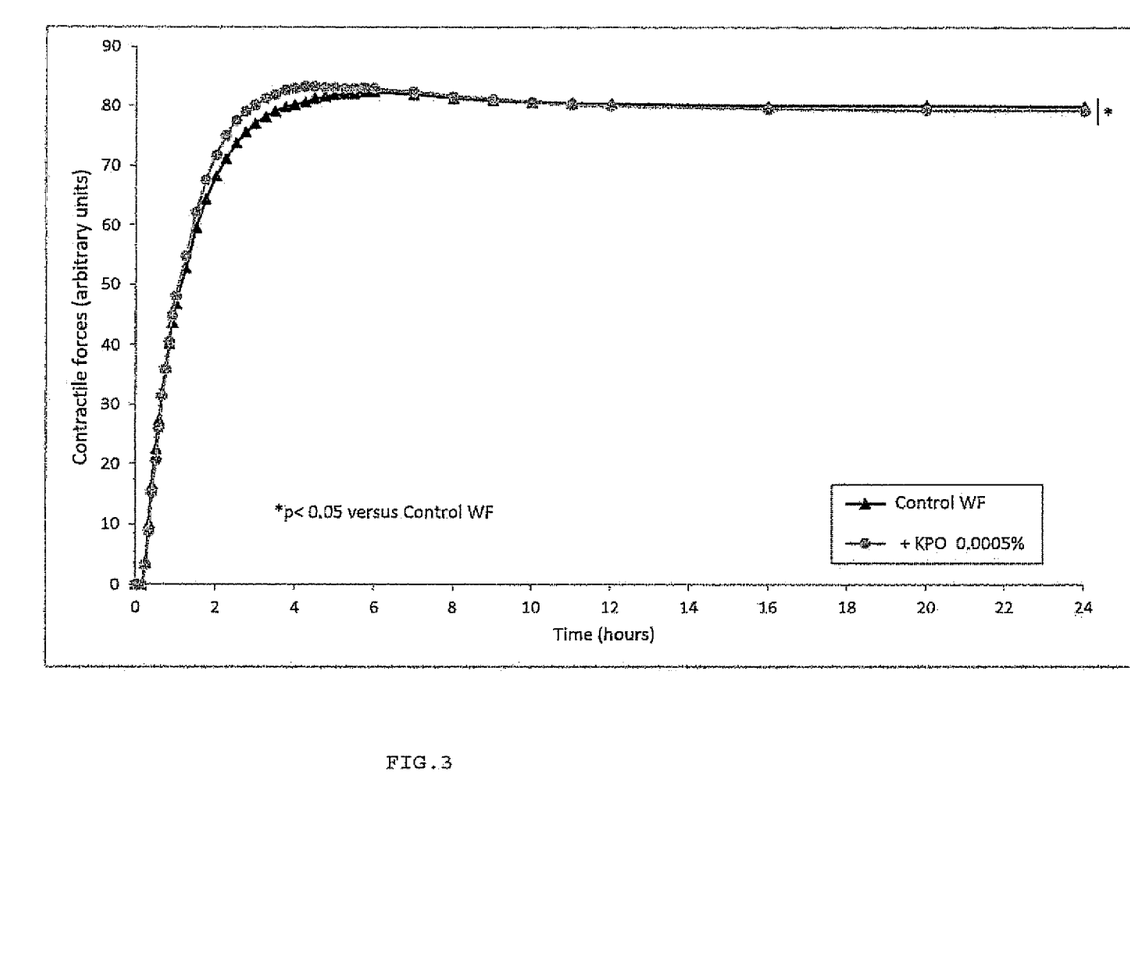
FIG. 3 represents the contractile forces developed by wrinkle fibroblasts (WF) in the presence or not of the KPO extract according to the invention.

The results are grouped together in FIGS. 1 to 3 and table 8. As expected, the contractile forces developed by the wrinkle fibroblasts (WF) are significantly reduced relative to those developed by healthy fibroblasts (HF).

In wrinkle fibroblasts (WF), the KPO extract at 0.0005% increased the contractile forces significantly. This result demonstrates an anti-wrinkle effect.

Applied to healthy fibroblasts, the KPO extract significantly increased the contractile forces. Analysis of the Glasbox® graphs shows that the AUC (area under the curve) and maximum contraction increased significantly in the presence of the extract. These results demonstrate a firming effect of the extract.

TABLE 8

| Analysis of GlasBox graphs (HF) | | | | |
|---|---|---|---|---|
| Parameters calculated | Control HF | | HF + 0.001% KPO | |
| | Mean | sem | Mean | sem |
| AUC | 2278.6 | 40.2 | 2574.5** | 101.1 |
| Max | 97.79 | 1.46 | 112.44** | 4.32 |

**p < 0.01 vs Control HF—One-factor Variance Analysis followed by a Fisher test

7—Evaluation of the Effect of KPO Extract on Mitochondrial Activity in Skin Fibroblasts Normal human dermal fibroblasts were incubated for 24 hours with KPO extract at 0.001% (d.e.). At the end of the treatment, the cells were collected by trypsination and incubated in the presence of an oxygen-sensitive fluorescent probe in order to measure oxygen consumption in real time by spectrofluorometry.

The results are grouped together in table 9. These results show that the KPO extract triggers and increase in overall respiration. Thus, the KPO extract triggers stimulation of the respiratory chain activity, an effect which is representative of stimulation of mitochondrial functions.

TABLE 9

| Measurement of oxygen consumption in NHDF | |
|---|---|
| | O2 consumption (%) |
| Untreated control | 100 |
| KPO at 0.001% | 145.40 |

The invention claimed is:

1. Cosmetic-method for treating dehydrated skin; skin with redness; elderly or photo-aged skin; photosensitive skin; cutaneous aging; and disorders related to radical attacks linked to chemical or atmospheric pollution, comprising administering to a subject in need thereof an effective amount of a polyphenol-rich extract of the Kapok tree flower comprising at least 15% by weight of polyphenols, relative to the total weight of the dry extract, at least 15% by weight of oligoproanthocyanidins (OPC), expressed as catechin equivalent, relative to the total weight of the dry extract, and at least 6% by weight of organic acids, relative to the total weight of the dry extract, wherein the Kapok tree is *Bombax costatum*.

2. The method of claim 1, wherein the extract further comprises at least 5% by weight of flavonoids, expressed as rutin equivalent, relative to the total weight of the dry extract.

3. The method of claim 1, wherein the extract is an extract of Kapok tree calyxes.

4. The method of claim 1, wherein the organic acids are alpha-hydroxy acids.

5. The method of claim 1, wherein the organic acids are acetic acid, malic acid, lactic acid, citric acid or mixtures thereof.

6. The method of claim 1, wherein the extract is obtained by solid/liquid extraction of the flowers of the Kapok tree in a solvent chosen from amongst binary mixtures of water/glycol.

7. The method of claim 6, wherein the solvent is chosen from amongst binary mixtures of water/glycol in a proportion comprised between 30 and 90% of glycol in water.

8. The method of claim 6, wherein the glycol is propanediol or propylene glycol.

9. The method of claim 1, wherein the cutaneous aging is photo aging.

\* \* \* \* \*